United States Patent [19]

Protell et al.

[11] 4,356,585
[45] Nov. 2, 1982

[54] HYGIENIC DENTAL APPLIANCE

[76] Inventors: Martin R. Protell, 215 E. 68th St., New York, N.Y. 10021; Howard L. Ward, 150 Central Park South, New York, N.Y. 10019

[21] Appl. No.: 252,166

[22] Filed: Apr. 8, 1981

[51] Int. Cl.³ .............................................. A46B 9/04
[52] U.S. Cl. ................................... 15/111; 15/167 R; 128/304
[58] Field of Search ................. 15/167 R, 167 A, 111, 15/110, DIG. 5; 128/304

[56] References Cited

U.S. PATENT DOCUMENTS

| | | | |
|---|---|---|---|
| 1,323,042 | 11/1919 | Gardner | 15/167 R |
| 2,028,519 | 1/1936 | Peterkin et al. | 15/167 R X |
| 2,083,217 | 6/1937 | Brothers et al. | 15/111 |
| 2,263,885 | 11/1941 | McGauley | 15/167 R X |
| 2,274,042 | 2/1942 | Cosby | 15/167 R |
| 3,254,356 | 6/1966 | Yao et al. | 15/111 |
| 3,742,549 | 7/1973 | Scopp et al. | 15/167 R |
| 4,274,174 | 6/1981 | Ertel | 15/167 R |

*Primary Examiner*—Peter Feldman
*Attorney, Agent, or Firm*—Lackenbach, Siegel, Marzullo, Presta & Aronson

[57] ABSTRACT

An improved dental appliance having an elongated handle portion including a tongue grooming region formed therein, a head portion having a plurality of discrete spaced bristle tufts extending therefrom in spaced relationship to each other, and wherein the head portion lies entirely below the longitudinal axis of the elongated handle. There is provided an offset connecting portion rigidly joining the head to the handle which is offset from the longitudinal axis of the handle and extends downwardly therefrom to a point below the level of the head and rigidly joins the handle with the head. The bristle tufts of the head are disposed in four longitudinal rows, and in a preferred embodiment the center two rows comprise stiffer bristles than those of the outer rows, are cut so as to form several wedge shaped crests when viewed from the side thereof, and extend above the level of the outer two rows. The tongue grooming region has formed therein a spoon-like shaped concave portion which is located within the ends of the handle and includes a rounded smooth curved lip which is adapted to be run along the upper surface of the tongue to remove any coating formed thereon.

7 Claims, 13 Drawing Figures

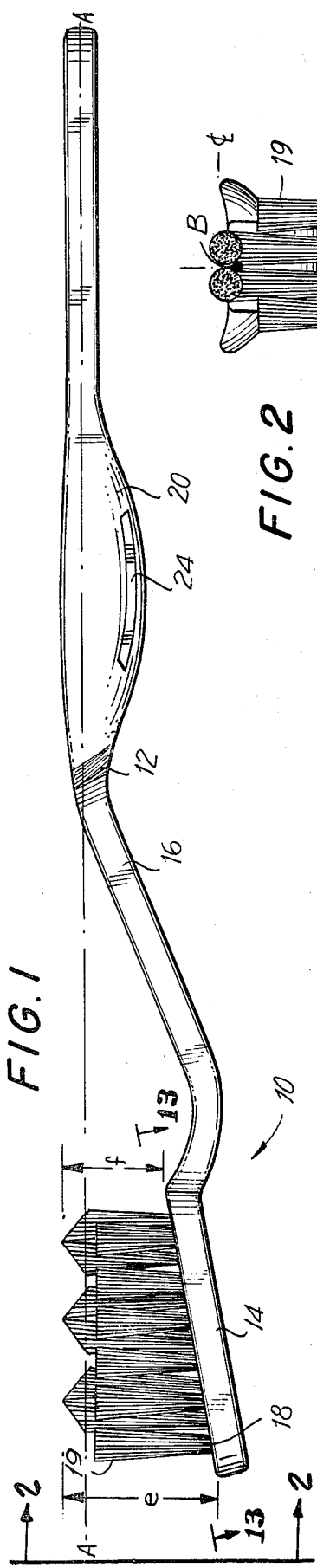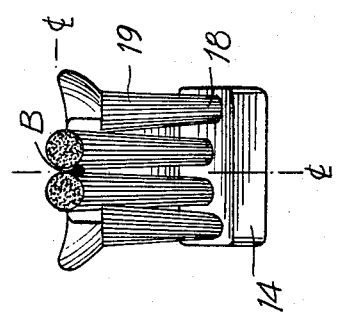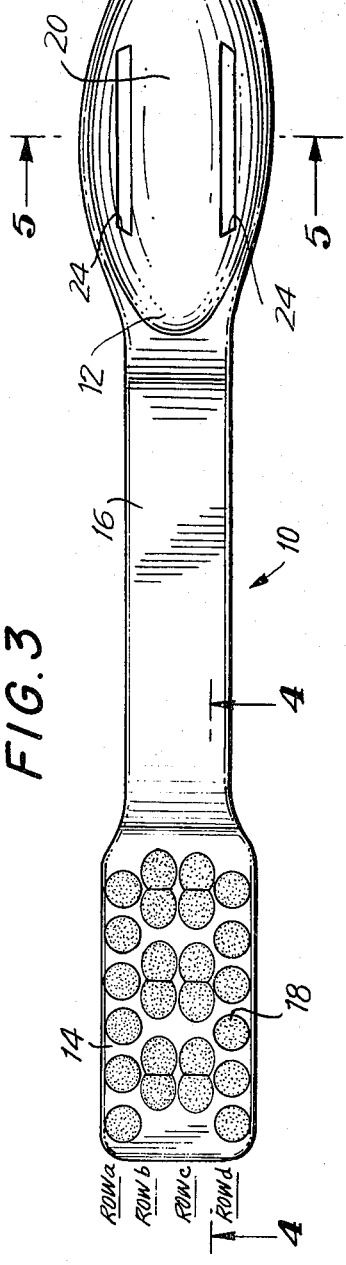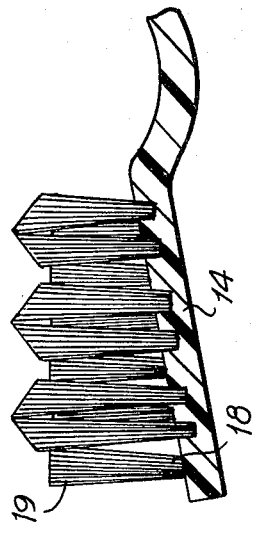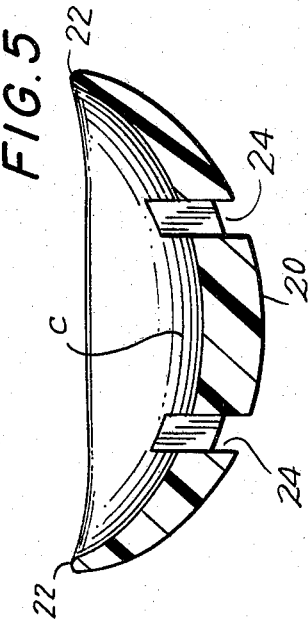

HYGIENIC DENTAL APPLIANCE

BACKGROUND OF THE INVENTION

The present invention relates to an improved dental instrument and more particularly to an improved configuration toothbrush and tongue groomer which is formed in the handle portion of the toothbrush and is adapted to safely and effectively massage and remove coating from the tongue surface. The configuration and structure of the joining portion between the handle and the head of the brush adapts the novel appliance for increased maneuverability to fit the head of the brush into normally difficult areas of the mouth to reach, and to allow the brush to be used with a minimum of displacement of the cheeks during brushing. The improved structural configuration and differing stiffness of certain bristle tufts adapt the present invention to be used with conventionally recognized brushing techniques to offer increased brushing action efficiency.

Disclosure Document No. 087,045 filed Jan. 4, 1980 is referred to herein, and a request is hereby made that it be incorporated into this application.

DESCRIPTION OF THE PRIOR ART

Various types of toothbrushes have been used in the past which incorporate a tongue treatment means. The following U.S. patents show various such configurations:

U.S. Pat. No. 2,049,956
U.S. Pat. No. 2,405,029
U.S. Pat. No. 1,658,706
U.S. Pat. No. De. 122,815
U.S. Pat. No. 2,574,654
U.S. Pat. No. 2,708,762
U.S. Pat. No. 3,254,356

As can be observed from the above-listed prior art U.S. patents, the tongue treatment tongue-scraping means in each case is not formed integral with the handle, such as can be seen in U.S. Pat. Nos. 2,708,762, 2,574,654, and U.S. Pat. No. De. 122,815.

Those prior patents showing a tongue scraping means formed by the handle, in all instances, form the scraper at one distal end of the handle, as can be seen in U.S. Pat. Nos. 2,049,516, 2,504,029, and 1,658,706. U.S. Pat. No. 3,254,356 shows a tongue scraper which is part of the handle, but which is considered ineffective and dangerous to use because of its straight edges.

Certain prior art patents show having an offset head such as the following U.S. Pat. No.: De. 162,941, U.S. Pat. Nos. 306,776, 2,651,068, and 1,741,143. However, the offset head would not facilitate easy brush manipulation as the head bends forwardly with respect to the handle.

As is readily apparent, the prior art does not show or suggest, taken singly or in combination, the structure of the present invention. Prior art brushes combining tongue scrapers are cumbersome as the tongue scraping portion hinders easy hand manipulation when using the bristles, and the bristles of such combined dental appliances are not adapted to facilitate different types of brushing techniques.

SUMMARY OF THE INVENTION

The present invention overcomes the disadvantages of prior art toothbrushes and tongue scrapers by providing a single medical appliance which incorporates significant improvements in connection with the structure and design of a toothbrush in combination with a tongue grooming portion. The human tongue frequently becomes coated not only from materia alba, saliva enzymatic digestion products, bacteria and food particles, but from internal secretions resulting from digestion which starts in the mouth, but also from exudates from the gingiva.

The present invention provides a therapeutic tongue cleaning device incorporated within the central portion of the toothbrush handle so that it does not hinder normal manipulation and handling of the toothbrush, all the while providing a readily accessable and readily handled structure for manually removing deleterious substances from the dorsum of the tongue, and thereby avoiding putrifaction and absorbtion or passage of such undesirable substances into the alimentary canal. Moreover, it has been found that regardless of the cleanliness of the teeth and gums, and the amount of mouthwash used, the human tongue with associated normal bacteria and the like, produces an odor which may only be effectively eliminated or controlled by the use of cleansing and removing such deleterious substances.

Those skilled and knowledgable in this art may recognize that brushing the teeth alone reduces mouth odor by only 25 percent, while grooming the tongue reduces mouth odor by 75 percent. When both operations are performed, odor can be reduced by 85 percent.

The toothbrush portion of the dental appliance features the crests of the free ends of the bristles being generally in longitudinal alignment with the longitudinal axis of the handle portion, and the provision of an offset connecting portion between the head and handle, rigidly connecting same. The connecting portion extends downwardly from the handle to a point below the level of the head (at least at the area of connection), and then extends upwardly to join with the head. The head portion accommodating the plurality of tufts of bristles is offset or disposed well below the longitudinal axis of the handle, providing an appliance featuring improved accessibility when brushing teeth; and requiring less space within the mouth so that the cheeks need not be greatly extended, retracted or agitated in order to brush rear teeth, thereby causing less irritation of the gums and abrading of the cheeks and allowing brushing while keeping the lips in relatively close engagement thereby almost eliminating undesired drooling during brushing. Moreover, the set back head design provides for improved accessibility in order to reach difficult surfaces. For example, the structure allows the head to be disposed over the occlusal surface to allow for accessibility to lingual or palatal tooth surfaces, marginal gingiva, and distal surfaces of the most posterier teeth.

The structure of the present invention also includes in combination an elongated handle portion including a therapeutic bulbous tongue grooming region formed therein and a head portion having a plurality of discrete bristle tufts extending from said head in spaced relationship to each other. The head portion is disposed entirely below the longitudinal axis of the handle and there is also provided an offset connecting portion rigidly joining said head to the handle. The offset portion extends downwardly from the longitudinal axis of the elongated handle to a point below the level of the head, at least at the area of connection, and extends upwardly to join with the head. The bristle tufts of the head are disposed in four longitudinal rows, the crests of the free ends of which form two substantially planar surfaces such that the two center rows extend above the level of the two outer rows and are preferably of a firmer bristle or in some other manner more resistant to bending or shear force. The outer rows of bristle tufts are preferably located near the edge of the head which helps reduce the overall size of the head. Moreover, in the preferred embodiment, the height of the bristles, in the longitudinal direction, increase progressively traveling away from the handle portion of the brush.

The structure of the present invention also includes a tongue grooming region disposed within the central portion of the handle which is a bulbous or wide concave region featuring two smooth curves, and the edges thereof being raised. There may be a plurality of cleaning apertures formed in the center thereof, which apertures facilitate cleansing and do not affect its cleaning function.

It is an object of the present invention to provide a dental appliance with improved accessibility and maneuverability within the mouth which may be easily handled and which will allow for the laymen to properly brush his teeth in all conventionally approved manners, with a minimum or no laceration or irritation of the gums, cheeks and soft tissues.

Moreover, it is an object of the present invention to provide a medical appliance which includes a tongue grooming region for performing a tongue cleaning operation thereby allowing for common bacteria and the like to be removed from the dorsum of the tongue and help effectively eliminate mouth odor.

Another object of the present invention is to provide a dental appliance having an improved bristle design wherein the center rows of bristles are raised above the level of the outer rows, may be disposed in non-parallel relationship to selectively lean toward one another, and are of a harder or more rigid substance, or which are of a larger diameter, so as to resist bending more than the bristles of the outer rows. Also, the center bristle tufts may be formed of bristles cut to form several wedge shaped crests as viewed laterally.

Yet still another object of the present invention is to provide a toothbrush structure adapted to reach and effectively clean those surfaces of the teeth in those areas of the mouth, which heretofore were inexcessable to toothbrushes of conventional design.

More specifically, it is an object of the present invention to provide a toothbrush configuration adapted to work around the shape of the human teeth, gums and jaws, allowing and facilitating bringing the major portion of the free ends of the bristles into proper engagement between the teeth and gums to more effectively clean and massage, using contemporary accepted dental techniques.

It is still a further object of the present invention to provide a toothbrush which may manually be disposed into the crevices between the teeth and provide efficient removal of foreign substances, which object may be obtained by having the height of the bristles in the longitudinal direction increase traveling from the handle, and which may be obtained effectively using the wedge shaped bristle crests of the inner bristle tufts.

It is also an object of the present invention to provide a toothbrush head design whereby the outer bristles are softer or more readily adapted to bend than the inner bristles, and may be used to gently dispose into the gingival sulcus. The inner bristles are of slightly greater height than the outer bristles and are used to reach the interproximal spaces.

It is still yet another object of the present invention to provide a bristle design wherein the tufts of bristles are staggered vis-a-vis the transverse direction of the head allowing the various tufts of differing firmnesses and lengths to simultaneously engage the surface of the teeth during the brushing operation.

Other objects of the present invention reside in the novel combination and arrangement of the toothbrush and tongue grooming apparatus such that both may be incorporated in the same appliance both economically and efficiently, and whereby during use the structure of each does not interfere with the normal manual manipulation of the other device, during the respective uses thereof.

Still further objects and features of the present invention reside in the provision of an improved dental device, which is simple in construction, inexpensive to manufacture, and thereby permits wide use and distribution.

These, together with the various ancillary objects and features of the invention which will become apparent as the following description proceeds, are obtained by the dental device disclosed herein, preferred embodiments of which are shown in the accompanying drawings, by way of example only, wherein:

BRIEF DESCRIPTION OF THE DRAWINGS

FIG. 1 is a side elevational view of the dental device made in accordance with the present invention;

FIG. 2 is a front elevational view thereof looking in the direction of 2—2 in FIG. 1;

FIG. 3 is a top plan view thereof;

FIG. 4 is a cross-sectional view thereof taken along the plane of 4—4 in FIG. 3;

FIG. 5 is a cross-sectional view thereof taken along the plane of 5—5 in FIG. 3;

DETAILED DESCRIPTION OF THE INVENTION

Figure 8:
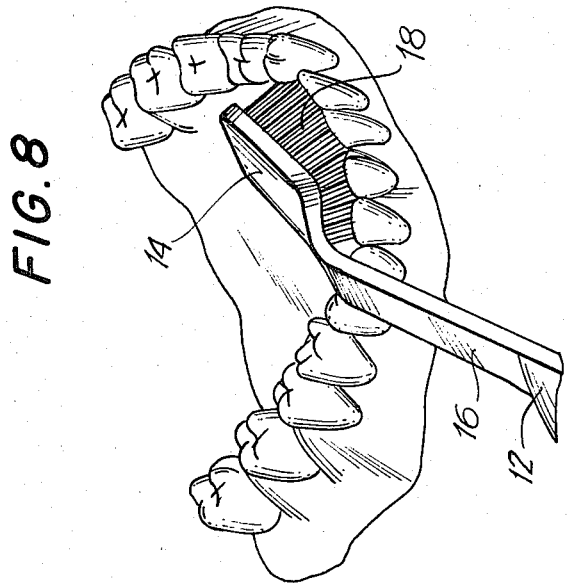
FIG. 8 is an exemplary view of the brush shown in use with the lingual surfaces of the front teeth.

With continuing reference to the accompanying drawings wherein like reference numerals designate similar parts throughout the various views, reference number 10 is used to generally designate the therapeutic medical device constructed in accordance with the concepts of the present invention. The medical appliance includes a handle portion 12* and a head portion 14 rigidly interconnected by way of an offset connecting portion 16 which rigidly connects the head 14 and handle 12 portions. The head 14 includes a plurality of discreet tufts of bristles 18 and the handle portion 12 incorporates an integrally formed tongue grooming member 20.

*The cross-sectional shape thereof may be as shown in the drawings, or of any desired cross-sectional shape, such as round, square, or octagonal, etc. The surface thereof may be smooth or roughened such as by serrations, or the like.

It is within the scope of the present invention that the entire handle 12, head 14 and connecting portion 16 be of unitary construction and of any suitable substantially rigid material such as plastic, or the like, which is preferably non-allergic after manufacture and which may be safely used in and around the human mouth. The basic structure of the appliance may be formed with any rigid material which will receive and retain the discrete tufts of bristles 18 and be readily formed to create the tongue grooming region 20. The bristles 18 may be of any natural or synthetic material, such as a flexible nylon filament, in the range of from 0.007 to 0.012 inch diameter, as will be more fully discussed and explained herein.

It is a feature of the present invention that the elongated handle 12 be substantially straight defining a longitudinal axis A—A which substantially coincides or falls within the planes formed by the free ends of the bristles 18 of the head portion 14. As seen in FIGS. 1 and 2, in a preferred embodiment, the bristles 18 are of various heights traveling longitudinally away from the handle portion, as well as being of different heights traveling transversely thereof. As regards the longitudinal direction, the various discrete rows a, b, c, and d of bristles 18 at the crests of the free ends form parallel surfaces such that an extension of the longitudinal axis of the handle would pass generally between the said planes through the imaginary point B as depicted in FIG. 2.

Figure 11:
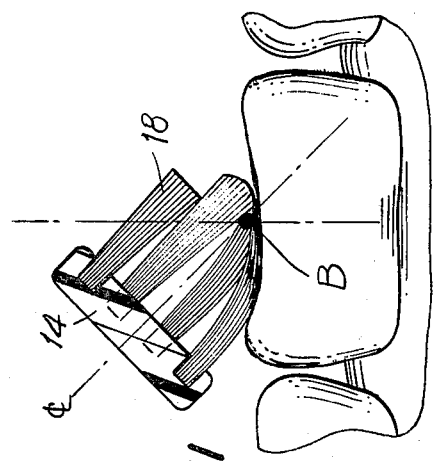
FIG. 11 depicts the center of rotation and action of the ends of the bristles of the present invention at the beginning of a manual rotation.
Figure 12:
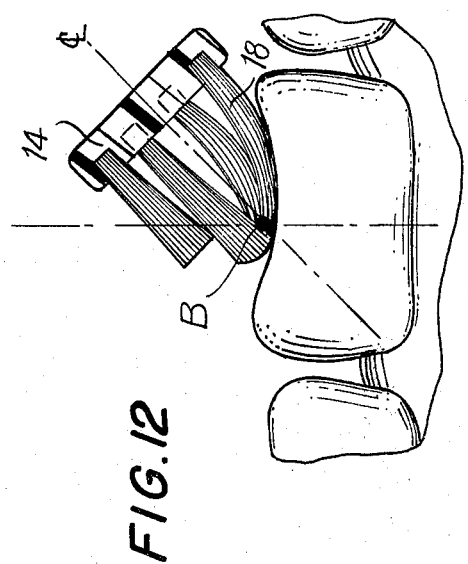
FIG. 12 corresponds to FIG. 11 and shows the ends of the bristles at the end of a manual rotation.
Figure 10:
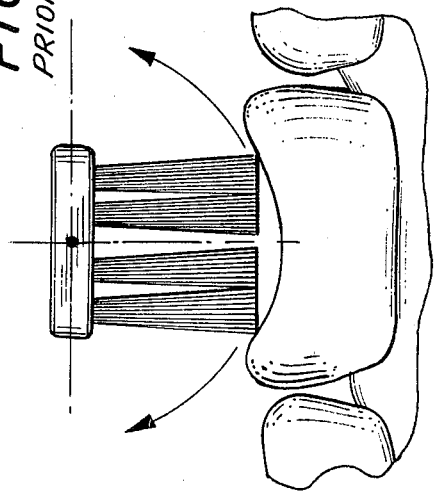
FIG. 10 depicts the center of rotation and sweeping action of the ends of the bristles across teeth utilizing a prior art toothbrush.

It has been found that considering the manner in which humans normally grasp and manipulate a substantially straight elongated handle, such as the handle portion 12 herein, that during a rotational movement, the easily controlled action of the bristles 18 when brushed across the teeth is different than the action of bristles when the center line of the handle passes through an imaginary point substantially near the retained ends of the bristles (as in the prior art). The advantageous and novel bristle action produced by rotating the handle is shown in FIGS. 11 and 12, and the different bristle action produced with prior art toothbrushes is depicted in FIG. 10, where the longitudinal axis of the handle is in alignment with the rigid head of the brush and the retained ends of the bristles.

In the preferred embodiment, there are four discreet longitudinal rows of bristles a, b, c, and d, which are comprised of spaced tufts 18 each being formed by a cluster of upstanding fibers or bristles 19 which are firmly anchored in the head 14 of the brush 10. The bristles 19 may be fabricated from natural bristle or synthetic materials, such as nylon or polypropylene and are non-allergic and capable of being sterilized by conventional means. The free ends of the bristles 19 may be rounded or end-polished, but such treatment of the ends of the bristles per se is not part of the present invention. However, the present invention encompasses the location and stagering of the bristle tufts 18, such as depicted in FIG. 3, such that each of the tufts 18 of the central rows b and c are disposed between the tufts of the outer rows a and d; and the tufts of the central rows b and c are in transverse alignment.

It is also within the scope of the present invention to provide a novel head design wherein the central rows of tufts b and c are for the most part longer than the outer two rows, and preferably the free ends are cut to form peaks or wedge shaped crest portions, and the central two rows of bristles tufts are comprised of bristles 19 that are of a firmer or stiffer nature than the bristles 19 of the outer rows a and d. The firmer or stiffer nature may be accomplished in a wide variety of ways, such as by utilizing bristles of a larger diameter, for the central two rows b and c, by picking a firmer or harder material for the bristles comprising rows b and c (than the bristles of rows a and d) or by incorporating more bristles within each tuft forming the inner two rows b and c, than are utilized to form the tufts of outer rows a and d.

One may readily appreciate that traveling longitudinally, the crest of the bristles of each discrete row a through d defines a planar surface, wherein the peaks of the inner two rows, b and c, are of equal height, and both form a planar surface. The outer two rows a and d are the same height and form a planar surface interrupted by the raised inner two rows.

It should be pointed out that the bristles tufts of longitudinal rows a and d are preferably located very near the edges of the head so that the head of the brush is as small as possible. The present invention, being an improved dental appliance, is being adapted to provide for increased accessability with respect to difficult areas of the teeth to clean, and only a minimum of head structure is required along the lateral edges of the head to retain the bristle tufts at their lower ends.

As clearly shown in FIG. 1, the central longitudinal rows b and c, when viewed from the side or laterally, preferably include bristles which are cut to form several peaks or crest portions. It is also within the scope of the present invention that the bristles forming the central two longitudinal rows b and c can be cut at their free ends to form a flat or planar surface*, but it has been found to be advantageous for the stiffer inner bristles to be formed into crest regions which are especially effective in dislodging particulate matter in interproximal spaces. The inner rows of tufts b and c cooperate effectively with the staggered arrangement of the outer rows, a and d, during brushing, as may be seen in FIG. 6. The inner bristles, during brushing, easily and readily extend outwardly between the bristles forming the outer rows.

*not shown

In order to form the peaked or crest portions, the bristles may be shaped by simply cutting the bristles to the desired configuration, the bristles being in conventional parallel relationship, or the tufts forming each crest or peaked region may comprise bristles which are disposed in non-parallel relationship such that they lean towards one another or converge at their free ends. By so leaning or angling the bristles, the uppermost portion of the crests would have the greatest density of bristles possible.

In the preferred embodiment, the longitudinal axis of the head 14 is not parallel to the longitudinal axis A—A of the handle, such that to bring the crests of the bristles 19 into substantial longitudinal engagement with the longitudinal axis of the handle A—A, the height of the bristles traveling in the longitudinal direction traveling away from the head are progressively longer. Accordingly, as the bristles at the outermost end of the head, dimension e, are longer than the bristles at the innermost portion of the head, dimension f, they are more readily bent, or offer less shear resistance, when brushed against the teeth, than the innermost portion.

The configuration of the present invention has been found to augment and increase the efficiency of the dental appliance 10, compared with conventional devices, in connection with most generally approved brushing techniques.

It is within the scope of the present invention that in order to create uniform stiffness across the free ends of the bristles 19, that either the number of bristles 19 in each tuft 18 traveling forwardly away from the handle 12 be increased, or stiffer or larger diameter bristles be utilized, such that the tufts 18 at their free ends generally offer equal shear resistance with the bristles at the innermost end.

Figure 6:
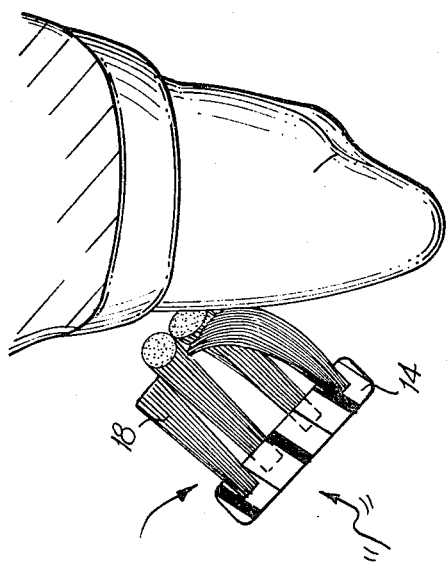
FIG. 6 is an exemplary view showing the head of the brush as used in connection with the teeth.

The head design of the brush, considering that the outer two rows a and d are reduced in height and are of generally softer bristles, is particularly adapted for a type of brushing technique wherein the edge of the brush is brought into engagement with the gingival sulcus and slightly vibrated or shimmied so as to simply wiggle or vibrate the ends of the bristles, or to roll or rotate the bristles about the gingival margin such that the bristles sweep the buccal surface of the teeth, as suggested in FIG. 6.

Figure 7:
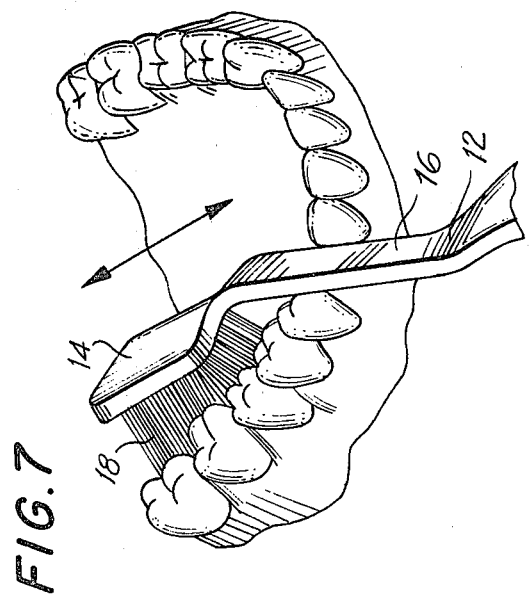
FIG. 7 is an exemplary view of the brush shown in use with the lingual surfaces of the rear teeth.

The present structure is also particularly suited for a scrub type brushing technique, such as depicted in FIG. 7, wherein the bristles are moved vis-a-vis the teeth in the direction of the longitudinal axis of the device. As those skilled in the art will appreciate, the outer bristles are particularly useful for engagement within the sulcus and will cause a minimum of laceration or abrasion thereof, whereas the stiffer interior bristles which are longer, during a sweeping or rolling type action, will extend through the spaces between the tufts of the outer rows, and extend into the interproximal spaces of the teeth and into the interproximal embrasures. The tufts of the inner rows b and c are so arranged to project between the tufts 18 of the softer exterior bristles (of rows a and d) to engage, debride, and dislodge adherent plack or foreign particles.

Due to the novel structure of the brush 10, the gums in normally inaccessible areas may be effectively massaged with the free ends of the softer bristles 19. Moreover, the maneuverability and accessibility, and advantageous action of the bristles, achieved by the novel design of the present invention, facilitates better cleaning of bridges and jacket crowns. The toothbrush 10 of the present invention enables efficient and effective bristle action on the teeth, but imparting less trauma and abrasion to teeth, gums, cheeks, and soft tissues within the mouth, compared with conventional toothbrushes.

The location of the head 14, in connection with the connecting portion 16, is offset or set back well below the longitudinal axis A—A of the handle 12, to a point below a portion of the head of the brush and possibly below the entire head portion 14. Such a set back head 14 is advantageous as the head 14 may readily be brought into normally difficult locations to clean within the mouth such as the lingual surfaces of the lower anterior teeth, the interproximal areas, the buccal, and lingual surfaces of the posterior teeth, such as exemplified in FIGS. 7 and 8.

The design of the free ends of the bristles 19 is such that using comfortable and natural manual manipulation, when the various conventionally approved dental brushing techniques are effected, (such as shimmying, rolling or rotation and scrubbing) the caries susceptible areas of the teeth, receive broad and uniform engagement with the free ends of the bristles 19. The particular design of the handle 12 and head 14 with the offset connecting portion 16 allows for a large area of the free ends of the bristles to be brought into firm engagement with the teeth situated in the midline of the mouth which are more susceptable to calculus than other surfaces.

The bristles 19 may be of a natural or synthetic material and have any convenient diameter such as from 0.007 to 0.012 inch; and in the preferred embodiment a variation of diameters may be used as explained herein. The bristles may be of conventional materials such as natural, or suitable synthetic polymer materials including nylon and the like.

It is readily appreciated by those skilled in the art that there is a correlation between the height of the bristles and the diameter thereof, which may be interworked to create a consistency or uniformity of stiffness at the free ends of all the bristles of the head.

The configuration and shape of the head in connection with the bristle arrangement described herein, results in reduced abrasion, erosion and decay of the teeth along the gingival lines. It should be appreciated that the bristles 19 are readily adapted to be pressed laterally against the teeth and a restricted longitudinal vibratory motion imparted thereto to produce a short anterior-posterior movement of the bristles, as well as adapted to clean with a limited movement in a direction toward and away from the occlusal plane. The present invention provides for increased bristle exposure to the teeth and gums, than the prior art, using such conventional brushing techniques.

The bristles during a rotation movement are caused to bow against the teeth and are thereby urged to enter the interproximal spaces where the ends of the stiffer inner bristles serve to dislodge accumulations therein while the ends of the softer outer bristles also cleanse the interproximal portions and gingival crevices of the teeth to which the brush is applied. The soft bristles serve to protect and massage the septal or interdental gum portions without causing undue injury thereto. Therefore, the present invention is particularly suited for most if not all presently preferred toothbrush type dental cleaning and brushing, including specifically vigorously massaging and stimulating interdental gum areas (interproximal embrasures) as well as the cervical area of the teeth and artifical restorations.

As those skilled in the art may appreciate, the head 14 of the brush 10 may be offset from, but parallel to, the longitudinal axis of the handle so that bristles of the same length traveling longitudinally would fall into substantial coincidence with an extension of the longitudinal axis of the handle, but in the preferred embodiment, the head is offset with respect to the longitudinal axis of the handle, such that as shown in FIG. 1. The length of the bristles closest to the handle, dimension f, as compared to the length of the bristles furthermost from the handle, dimension e, may be as much as 90% shorter, and the present invention preferrably envisions differences in height from 5 to 80%, from 15 to 60% and preferrably approximately 50% shorter, depending upon the size of the head.

The offset connecting portion 16 is a primary feature of the present invention and adapts the appliance to be disposed over teeth to reach interior portions for cleaning by the bristles 19, such as shown in FIGS. 7 and 8, and furthermore allow the ends of the bristles, considering comfortable manipulation of the handle, to be used with a maximum of maneuverability. As shown in FIGS. 11 and 12, the bristles are both bent or bowed against the teeth, and the springlike action used effectively, and not as in a prior art sweeping manner, such as depicted in FIG. 10.

Formed within the handle 12 of the brush, is a tongue grooming portion 20 of substantially concave shape, and which have a raised lip portion 22 as shown in FIG. 5. It has been found that it is impossible to effectively control or eliminate mouth odor by only cleaning teeth, either by the use of a dentrifice or mouthwash. Such will not effectively clean or remove the bacteria, and the like, found within the normal coating of the surface of the tongue. Moreover, as routine tongue grooming has been found to be beneficial, such grooming may be efficiently and safely effected by the layman by the use of the tongue cleaning portion 20 formed within the handle of the toothbrush 10.

Figure 9:
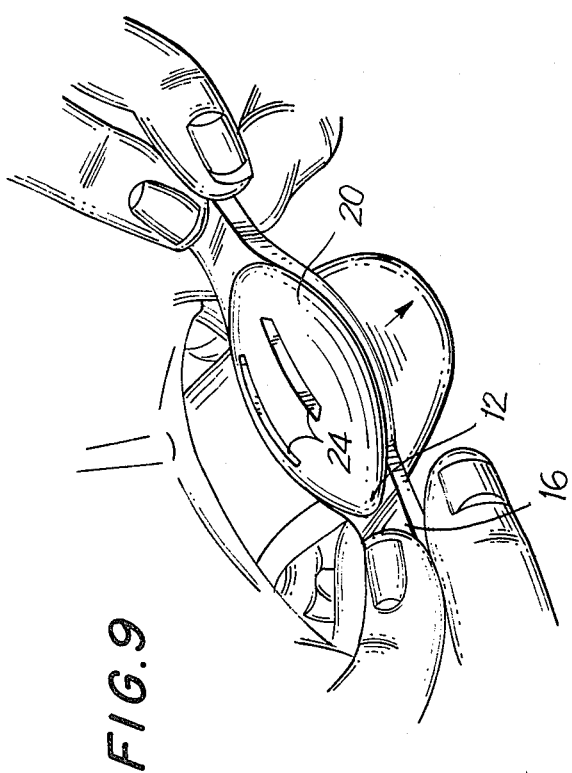
FIG. 9 is a exemplary view showing the tongue grooming portion in use with the tongue.
Figure 13:
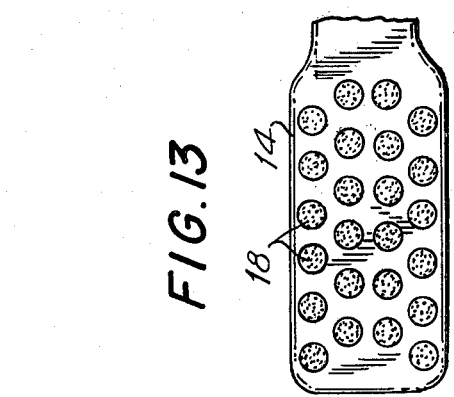
FIG. 13 is a cross-sectional view taken along the plane of 13—13 in FIG. 1.

It firstly must be appreciated that the location of the tongue grooming portion 20, within the central portion of the handle 12, is quite significant. When the toothbrush is held for brushing (by gripping it between the thumb and forefinger, and/or middle finger), the enlarged spoon shaped portion 20 falls within the palm of the hand of the user and does not in any way hinder manual manipulation of the brush. Moreover, as shown in FIG. 9, the tongue grooming portion may be used by grasping the handle at the end opposite the head of the brush, and the offset connecting portion, so as to bring one of the smooth curved shaped lips 22 of the tongue grooming portion 20 along the dorsum of the tongue by moving it along the longitudinal axis of the muscle.

The tongue grooming portion 20 is preferrably concave so that the material safely scraped from between the papillae and grooves on the upper surface of the tongue accumulates in region C. There may be preferrably, a plurality of apertures or slots 24 formed within the region so the accumulated mass cleaned from the tongue may be readily rinsed or cleaned by holding the appliance 10 under the faucet whereby the accumulated mass is forced by running water to flow through the slots into the sink, or to allow water to be forced into the portion 20 from the convex side.

The shape of the edges 22 of the tongue grooming portion 20 define smooth curves whereas the entire region is somewhat elliptical in shape, and the edges, which are intended to be brought into engagement with the upper surface of the tongue have a polished and rounded smooth edge, to avoid abrasion or irritation to the surface of the tongue.

It is the object of the edges 22 of the tongue groomer 20 to remove deposits within the minute crevices of the tongue, but not to lacerate or otherwise injure the dorsum surface.

The present invention is readily utilized as a tongue groomer by repeatedly moving the grooming portion longitudinally along the upper surface of the tongue, traveling outwardly away from the oral cavity, and the device may be easily manipulated without having to grasp the bristles of the brush.

The design of the present invention is not to be confused with conventional toothbrushes which do not incorporate the combination of a tongue grooming portion in connection with improvements in both the bristle and head design of the toothbrush, as well as the disposition of the head with respect to the longitudinal axis of the elongated handle.

The individual regions of the brush, such as the head 14 or handle 12, may be adapted to accommodate conventional structures such as a pointed rubber gum massager affixed to the end of the handle 12, or a snap on, or slip on cover, to surround and protect the bristles 19 of the head portion 14. Such conventional features would not interfere with the basic structure or therapuetic performance with its associated improvements over the prior art, and would compliment the brush.

The device may be manufactured using conventional techniques, including conventional forming of the bristle tufts, and the entire device may be of a non-allergenic material that is capable of being sterilized utilizing sterilizing gases, radiation or suitable heat and pressure as desired.

A latitude of modification, substitution and change is intended in the foregoing disclosure, and in some instances, certain features of the present invention may be employed without a corresponding use of other features.

We claim:

1. A dental appliance comprising an elongated handle portion including a tongue grooming region formed therein, a head portion having a plurality of discrete bristle tufts extending from said head in spaced relationship to each other, said head portion being entirely disposed below the longitudinal axis of said handle, and an offset connecting portion rigidly joining said head to said handle such that such connecting portion extends downwardly from the longitudinal axis of said elongated handle to a point below the level of said head and extends upwardly to join with said head, said bristle tufts of said head being in four longitudinal rows, the free ends of said bristles of the two center rows forming a planar surface and extending above the uppermost point of the free ends of the two outer rows, the longitudinal plane of the head being not parallel to the longitudinal axis of said handle such that the end of said head furthest from the handle is lower than the end which is closer thereto, and the bristle tufts being of unequal length such that the bristles are progressively longer traveling away from said handle and the free ends thereof are substantially in alignment with the longitudinal axis of said handle.

2. A dental appliance as in claim 1, wherein the bristles of the inner two rows are of a stiffer material than the bristles of the outer two rows.

3. A dental appliance as in claim 1, wherein the bristle tufts of the inner two rows are not in transverse alignment with the bristle tufts of the outer two rows.

4. A dental appliance as in claim 1, wherein the bristle tufts of the inner two rows are disposed in selective non-parallel relationship.

5. A dental appliance as in claim 1, wherein the inner two rows of bristle tufts are cut to form several discrete wedge shaped portions when viewed laterally.

6. A dental appliance as in claim 1, wherein said tongue grooming portion is a bulbous region located within the ends of the handle portion and has at least one elongated slot therein.

7. A dental appliance as in claim 1, wherein the edges of said tongue grooming portion comprise a raised lip of rounded smooth shape and define a smooth curved portion, and the lip faces in the direction of the bristles.

* * * * *